United States Patent
Duong et al.

(10) Patent No.: US 12,383,492 B2
(45) Date of Patent: Aug. 12, 2025

(54) COATINGS FOR BIOLOGICAL INTERFACE ON IMPLANTS

(71) Applicant: Battelle Memorial Institute, Columbus, OH (US)

(72) Inventors: Anthony D. Duong, Columbus, OH (US); Erik W. Edwards, Gahanna, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 915 days.

(21) Appl. No.: 17/043,220

(22) PCT Filed: Apr. 2, 2019

(86) PCT No.: PCT/US2019/025290
§ 371 (c)(1),
(2) Date: Sep. 29, 2020

(87) PCT Pub. No.: WO2019/195216
PCT Pub. Date: Oct. 10, 2019

(65) Prior Publication Data
US 2021/0007974 A1    Jan. 14, 2021

Related U.S. Application Data

(60) Provisional application No. 62/651,360, filed on Apr. 2, 2018.

(51) Int. Cl.
| | | |
|---|---|---|
| *A61K 9/00* | (2006.01) | |
| *A61K 31/437* | (2006.01) | |
| *A61K 31/573* | (2006.01) | |
| *A61K 35/16* | (2015.01) | |
| *A61K 38/18* | (2006.01) | |
| *A61K 38/19* | (2006.01) | |
| *A61K 38/30* | (2006.01) | |
| *A61L 27/34* | (2006.01) | |
| *A61L 27/54* | (2006.01) | |
| *A61L 27/58* | (2006.01) | |

(52) U.S. Cl.
CPC .......... *A61K 9/0024* (2013.01); *A61K 31/437* (2013.01); *A61K 31/573* (2013.01);
(Continued)

(58) Field of Classification Search
None
See application file for complete search history.

(56) References Cited

U.S. PATENT DOCUMENTS

2005/0271696 A1   12/2005   Dinh et al.
2006/0229711 A1*  10/2006   Yan ..................... A61F 2/82
                                                  623/1.38
(Continued)

FOREIGN PATENT DOCUMENTS

WO   WO 2010/059348 A1   5/2010
WO   WO 2017/165651      9/2017

OTHER PUBLICATIONS

Bacakova, Lucie et al., Modulation of cell adhesion, proliferation and differentiation on materials designed for body implants, Biotechnology Advances, Feb. 15, 2011, pp. 739-767, Elsevier Inc.
(Continued)

*Primary Examiner* — Kyung S Chang
(74) *Attorney, Agent, or Firm* — Lippes Mathias LLP

(57) ABSTRACT

Disclosed herein are coatings made from a biocompatible controlled release polymer and an active component. The active component can be, for example, an antimicrobial agent, an immune modulating agent, a cell signaling factor, or a growth factor. The coating has micrometer and nanometer scale features on the surface thereof.

14 Claims, 3 Drawing Sheets

(52) U.S. Cl.
CPC .......... *A61K 35/16* (2013.01); *A61K 38/1825* (2013.01); *A61K 38/1841* (2013.01); *A61K 38/185* (2013.01); *A61K 38/1875* (2013.01); *A61K 38/1891* (2013.01); *A61K 38/19* (2013.01); *A61K 38/193* (2013.01); *A61K 38/30* (2013.01)

(56) References Cited

U.S. PATENT DOCUMENTS

2009/0093879 A1* 4/2009 Wawro ................. A61F 2/0077
623/11.11
2015/0158051 A1* 6/2015 Hoerr ....................... B05D 1/06
427/2.1

OTHER PUBLICATIONS

Lv, Junping et al., Controlled release of vancomycin hydrochloride from a composite structure of polymeric films and porous fibers on implants, Chemical Engineering Journal, Feb. 13, 2017, pp. 601-610, Elsevier Inc.

Shah, Nisarg J., Osteophilic Multilayer Coatings for Accelerated Bone Tissue Growth, Adv Mater. Mar. 15, 2012, pp. 1-11, NIH Public Access.

Sirinrath, Sirivisoot et al., Electrically controlled drug release from nanostructured polypyrrole coated on titanium, Nanotechnology, Jan. 17, 2011, IOP Publishing, UK & the USA.

International Search Report dated Jul. 9, 2010 from PCT/US2019/025290.

* cited by examiner

COATINGS FOR BIOLOGICAL INTERFACE ON IMPLANTS

CROSS-REFERENCE TO RELATED APPLICATIONS

This application is a 371 of PCT/US2019/025290, filed Apr. 2, 2019, which claims priority to U.S. Provisional Patent Application Ser. No. 62/651,360 filed on Apr. 2, 2018, the contents of which are fully incorporated by reference herein.

BACKGROUND

The present disclosure relates to the design of coatings for medical implants, such as hardware associated with orthopedic knee and hip replacements. The coatings include a surface with surface features thereon. The surface features stimulate the adhesion and integration of cells such as osteoblasts to produce new autologous material at the implant interface. The coatings also contain active components whose release rate can be controlled as desired.

When the implants for a joint (knee or hip) replacement are implanted, there is a "race to the surface" in which osteoblasts (bone generating cells) and bacterial cells compete to colonize the surface of the new implants. If the osteoblasts prevail (known as osseointegration) and produce bone material (osteoinduction), the interface between the implant and the natural bodily system is much more favorable. However, if the bacterial cells prevail, a biofilm forms on the implant and infection results. These biofilms are difficult to penetrate and treat with antibiotics. As a result, a second surgery (known as a revision surgery) may be needed in which the original implant is removed, a temporary spacer is inserted, the infection is cleansed through rinsing and abrasion (debridement), antibiotics are administered to clear the infection, and then a new implant is placed. The entire revision surgery process can require 6-8 weeks, during which time the patient is immobile. It would be desirable to provide implants that favor the growth of osteoblasts and retard the growth of bacterial cells.

BRIEF DESCRIPTION

The present disclosure relates to coatings for medical implants or prostheses. The coatings have a micro structured surface, i.e. surface features, that stimulate osseointegration. The coatings also have a controlled release capability for releasing active components, such as antimicrobial agents for providing sustained bacterial kill or other active compounds intended to enhance osseointegration. Such coatings offer faster recovery time and reduced invasiveness during revision surgeries.

Disclosed in various embodiments herein are coatings having a surface with features thereon, the coatings comprising a biocompatible controlled release polymer and at least one active component.

The features include micrometer scale features and nanometer scale features. In some embodiments, the features are made by embossing a pattern into the surface. In other embodiments, the features are made by depositing fibers onto the surface of the coating.

The biocompatible controlled release polymer can be a silicone, a polyester, a polysaccharide, or a polyethylene glycol functionalized methacrylate.

At least one active component can be an antimicrobial agent, an immune modulating agent, a cell signaling factor, or a growth factor. In particular embodiments, a plurality of different active components is present in the coating. The antimicrobial agent can be an aminoglycoside; a glycoside antibiotic; a macrolide; a nitroimidazole; a tetracycline; a cephalosporin; a quinolone; a sulfonamide; a cyclic lipopeptide; a glycylcycline; an oxazolidinone; or a lipiarmycin. The immune modulating agent can be imiquimod, resiquimod, or dexamethasone. The cell signaling factor can be a cytokine. The growth factor can be derived from platelet rich plasma; or can be adrenomedullin; angiopoietin; a bone morphogenic protein (BMP); a colony stimulating factor (CSF); an epidermal growth factor (EGF); a fibroblast growth factor (FGF); a glial cell line-derived neurotrophic factor (GDNF); an insulin-like growth factor (IGF); or a transforming growth factor (TGF).

Also disclosed are methods of forming a coating having a surface with features thereon, comprising: forming a coating upon a substrate; the coating comprising a biocompatible controlled release polymer and at least one active component; and applying features to a surface of the coating.

The features can be applied by embossing a pattern into the surface of the coating. The features can also be applied by anisotropic etching of the surface or by isotropic etching of the surface, for example by using a patterned template. The features could be applied by 3D printing or other printing techniques. The features can alternatively be applied by depositing fibers onto the surface of the coating. In particular embodiments, the fibers are also made of the biocompatible controlled release polymer present in the coating. The substrate can be the surface of an implant.

The coating can be formed by depositing a layer that comprises the biocompatible controlled release polymer and the at least one active component dispersed therein. Alternatively, the coating can be formed by depositing a plurality of layers upon the substrate, with at least one layer containing at least one active component, and a layer that comprises the biocompatible controlled release polymer forming the surface of the coating.

Also disclosed herein are medical implants having a surface with a coating thereon, the coating having a surface with features thereon, and the coating comprising a biocompatible controlled release polymer and at least one active component.

These and other non-limiting aspects of the disclosure are more particularly discussed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
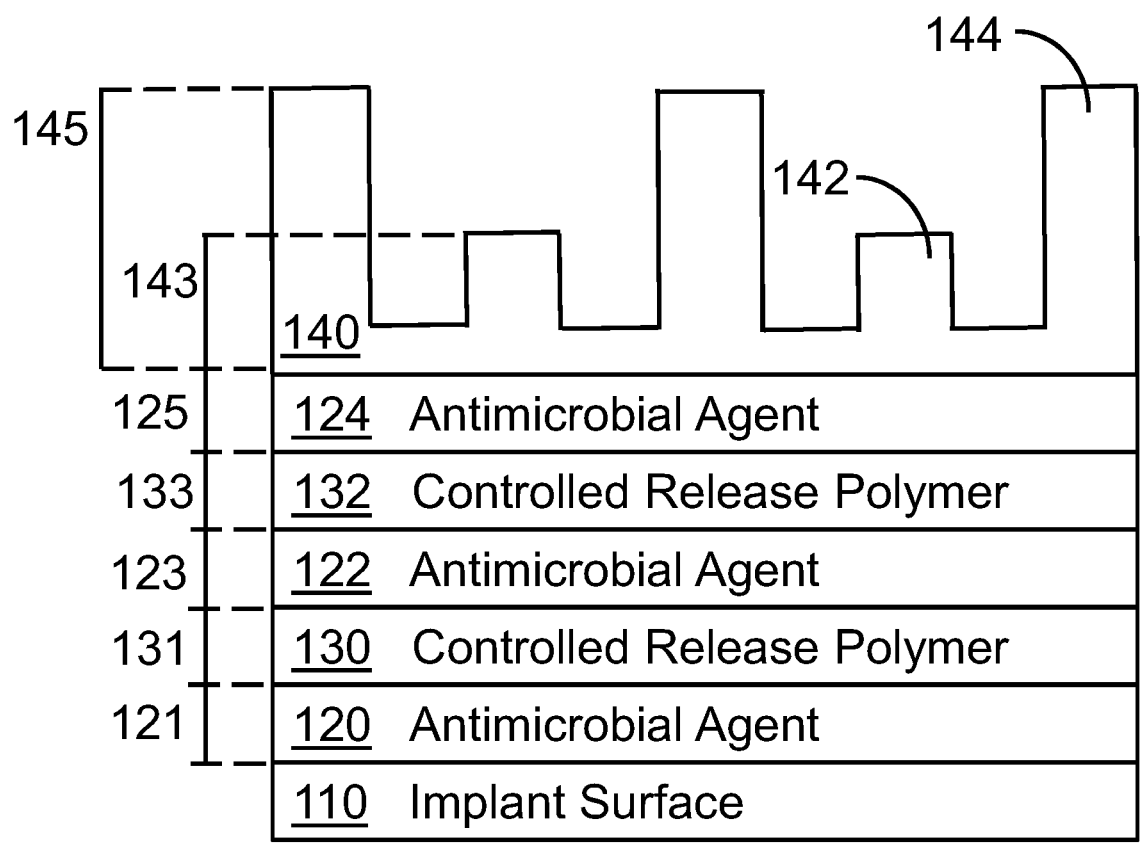
FIG. 1 is a cross-sectional view of a first example embodiment. The coating comprises a plurality of controlled release layers and a plurality of layers containing active components. Surface features are embossed into the outer layer.

A more complete understanding of the methods and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number.

The term "alkyl" refers to a linear or branched array of atoms that is composed exclusively of carbon and hydrogen. The array of atoms may include single bonds, double bonds, or triple bonds. Alkyl groups may be substituted or unsubstituted. Exemplary alkyl groups include methyl, ethyl, and isopropyl.

The term "aryl" refers to an aromatic radical composed entirely of carbon atoms and hydrogen atoms. When aryl is described using a numerical range of carbon atoms, substituted aromatic radicals are not included. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "fiber" refers to a strand of material having a length and a diameter, generally having a cylinder-like shape. The length is greater than the diameter. The fibers may have an average diameter of from about 1 micron to about 40 microns. The fibers may also be described as having these recited average diameters and also having an aspect ratio (length to diameter) of from about 3:1 to about one million:1.

The present disclosure relates to coatings intended for medical implants. The coating comprises a biocompatible controlled release polymer and at least one active component. The coating has surface features that stimulate the adhesion and integration of bodily cells, such as osteoblasts, to produce new autologous material at the surface of the implant.

The coating comprises a biocompatible controlled release polymer. The term "biocompatible" refers to the fact that the polymer does not have toxic or injurious effects when implanted in the body. The term "controlled release" refers to the ability of the polymer to release active components at a rate suitable for an effective dosage to be provided over a time period of at least 3 weeks, although preferably for longer time periods, such as 8 weeks or more.

The biocompatible controlled release polymer will release active components over time, for example through biodegradation or through diffusion. In some embodiments, this controlled release can be achieved in a sustained manner through a swelling, diffusion mechanism. For example, the polymer could be a silicone polymer that absorbs water in physiological conditions. As the water diffuses into the silicone, the antimicrobial active agent diffuses out through the water-filled matrix. Such silicone or siloxane polymers are of the general formula $(SiR_2O)_n$, where each R is independently hydrogen, alkyl, or aryl. The release rate can be tuned by changing the polymer chemistry, molecular weight, etc. Hydrophilicity could also be obtained by incorporating bioinert hydrophilic monomers such as hyaluronic acid or polyacrylic acid into the silicone polymer.

In other embodiments, the controlled release polymer may be a bioresorbable polymer that is hydrolyzed and dissolves under physiological conditions (e.g. temperature, pH) at a rate that can be tuned by changing the polymer chemistry, molecular weight, and blend. As the polymer degrades, the active components(s) are released. The polymer acts as a matrix in which the active component(s) are retained. Examples of such bioresorbable polymers include: polyesters such as poly(lactic-co-glycolic acid) (PLGA) or poly (ortho ester)s; or polysaccharides such as dextran; or polyethylene glycol functionalized methacrylates. In addition, bioresorbable polymers may act as a scaffold for autologous cells and then biodegrade once sufficient bone or extracellular matrix has been regenerated. More generally, the polymer may be a thermosetting polymer or a cured polymer. It has been determined, however, that hydroxyapatite (HA) is not a suitable material for the biocompatible controlled release polymer because its release profile is too fast, i.e. it releases active components too quickly to achieve sustained bacterial kill.

The coating also comprises at least one active component. The active component can be an antimicrobial agent, an immune modulating agent, a cell signaling factor, nutrient, antioxidant, or a growth factor. It is noted that there may be some overlap between some of these categories of active components. In some embodiments, multiple active components are used. The proximity of the coating to the surface of the medical implant permits the release dosage of the active component(s) to be low and still provide local delivery to the implant surface.

Antimicrobial agents are used to stop bacterial growth and reduce/prevent the formation of a biofilm on the medical implant. The term "antimicrobial" is intended to encompass antibiotics and microbicides (which kill bacteria), and bacteriostatic agents (which stop bacteria from reproducing). For antimicrobial agents, a low dosage release rate due to the proximity of the coating to the medical implant surface reduces infection while also mitigating the risk of antimicrobial resistance. In addition, the presence of antimicrobial agents could prevent infection from arising when the coating is used on the primary implant, thus preventing the need for revision surgery at all. Examples of antimicrobial agents that can be used include aminoglycosides such as gentamicin or neomycin; glycoside antibiotics such as vancomycin; macrolides such as azithromycin; nitroimidazoles such as metronidazole; tetracyclines such as doxycycline; cephalosporins; quinolones; sulfonamides; cyclic lipopeptides such as daptomycin; glycylcyclines such as tigecycline; oxazolidinones such as linezolid; and lipiarmycins such as fidaxomicin. Desirably, antimicrobial agents are released at a near linear (i.e. constant) rate over a period of about 3 weeks to about 8 weeks. Desirable release rates for antimicrobial agents (amount over time) are those sufficient to reduce or prevent infection.

Immune modulating agents can be used to reduce scarring and improve the natural immune system response at the interface between the implant and the body. Examples of immune modulating agents include immune-stimulants such as imiquimod and resiquimod, or immune-suppressants such as dexamethasone. Desirably, immune modulating agents are released at a near linear (i.e. constant) rate over a period of about 3 weeks to about 8 weeks. Desirable release rates for immune modulating agents are those sufficient to reduce or prevent scarring or to invoke an immune system response.

Cell signaling factors and growth factors can be immobilized on the surface of the coating to induce the production of autologous tissue, such as new bone. They can signal osteogenic cells to differentiate and/or produce bone material once integrated into the surface morphology of the coating. Examples of cell signaling factors include cytokines such as interferon, interleukin, and tumor necrosis factor. Examples of growth factors include platelet-rich-plasma derived growth factors; adrenomedullin; angiopoietin; bone morphogenic proteins (BMP); colony stimulating factors (CSF); epidermal growth factors (EGF); fibroblast growth factors (FGF); glial cell line-derived neurotrophic factors (GDNF); insulin-like growth factors (IGF); and transforming growth factors (TGF). Desirably, these factors are released at a near linear (i.e. constant) rate over a period of about 3 weeks to about 8 weeks. Desirable release rates for these factors are sufficient to induce autologous tissue production, induce differentiation, or to produce bone material.

A nutrient is, broadly, any substance that is used by a cell to survive, grow, and/or reproduce. However, for purposes of the present disclosure, a "nutrient" is an energy source, amino acid, protein, fatty acid, vitamin, or mineral as listed in this paragraph. Energy sources considered to be a nutrient are monosaccharides or disaccharides such as glucose, fructose, or lactose. Amino acids considered to be a nutrient are phenylalanine, valine, threonine, tryptophan, methionine, leucine, isoleucine, lysine, and histidine. Proteins which provide these amino acids are considered to be a nutrient. Fatty acids considered to be a nutrient are alpha-linolenic acid and linoleic acid. Vitamins considered to be a nutrient are vitamins A, C, D, E, K, thiamine, riboflavin, niacin, pantothenic acid, B6, biotin, folate, and B12, or precursors thereof, in any of their forms. Minerals considered to be a nutrient are sulfur, potassium, chlorine, sodium, calcium, phosphorus, magnesium, iron, zinc, manganese, copper, iodine, chromium, molybdenum, selenium and cobalt, including molecules which can provide these minerals. Desirably, these nutrients are released at a near linear (i.e. constant) rate over a period of about 3 weeks to about 8 weeks. Desirable release rates for these nutrients are sufficient to induce growth or reproduction of desired cells such as osteoblasts.

An antioxidant inhibits the oxidation of other molecules, reducing the formation of free radicals. Antioxidants include alpha lipoic acid, beta carotene, cysteine, gluthathione, hydrogen peroxide, resveratrol, vitamin A, vitamin C, vitamin E (including tocotrienols and tocopherols), uric acid, melatonin, astaxanthin, lutein, lycopene, flavonoids, phenolic acids, carotenoids, and selenium. It is noted that there is significant overlap between "nutrient" and "antioxidant" as used in the present disclosure, but that overlap is not complete. Desirably, antioxidants are released at a near linear (i.e. constant) rate over a period of about 3 weeks to about 8 weeks. Desirable release rates for these antioxidants are sufficient to perform the antioxidant function.

The coating can be formed by a layer-by-layer (LbL) deposition technique. Generally, alternating layers of materials are deposited upon a substrate to build up the coating. Different layers will contain the active component(s), while the biocompatible polymer is applied as a separate layer. This immobilizes the active component on the surface of the implant. The multilayer buildup of the coating can be based on electrostatic attraction/repulsion, hydrophobic attraction/repulsion, and combinations of such forces between adjacent layers. This deposition technique permits a high degree of control over the thickness of each layer.

Alternatively, the active component(s) may be in the form of a powder, emulsion, or solution that is dispersed in a water absorbing polymer, which is then applied to form the coating. The active component(s) will dissolve and diffuse out of the water absorbing polymer upon exposure to water.

Alternatively, the active component(s) may be in the form of a powder, emulsion, or solution that is dispersed in a hydrolyzable polymer, which is then applied to form the coating. The active component(s) will dissolve and diffuse out when the polymer is hydrolyzed.

The coating has microstructured surface features. Put another way, the surface has micrometer scale and nanometer scale features that rise above an outermost surface of the coating. These rough surfaces stimulate osseointegration at the surface and favor osteoblast adhesion. The term "micrometer scale" refers to features that have a height of 1 micrometer to less than 1000 micrometers. The term "nanometer scale" refers to features that have a height of 1 nanometer to less than 1000 nanometers (i.e. 1 micrometer). These surface features can be in the form of a regular pattern on the surface, or they can be stochastically (i.e. randomly) located. These surface features are exposed, which allows for the immediate colonization thereof by, for example, osteoblasts in parallel with the release of active components.

In some embodiments, this surface structure can be generated by embossing a pattern onto the surface of the polymeric coating via a mold technique. This embossing generally occurs after the controlled release polymer and active components are applied to the implant surface. The surface features could also be formed by etching (anisotropic or isotropic) or by 3D printing, or by other printing techniques.

In other embodiments, the surface structure may be achieved by an electrospinning technique. Very generally, the biocompatible controlled release polymer is spun into fibers through an electrohydrodynamic jet and precipitated onto the surface of a grounded target implant.

Figure 2:
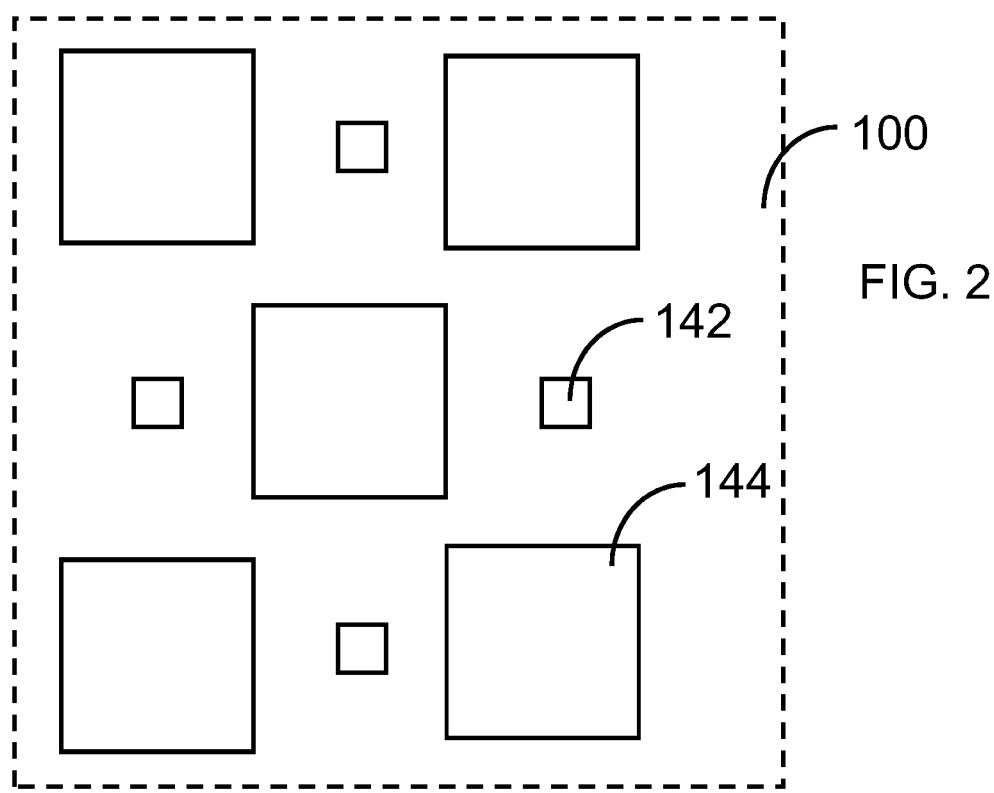
FIG. 2 is a plan view of the coating of FIG. 1.

FIG. 1 and FIG. 2 show one example embodiment of the present disclosure. FIG. 1 is a illustrative cross-sectional view, and FIG. 2 is a plan view.

Turning first to FIG. 1, in this embodiment, the implant surface 110 serves as a substrate upon which several layers are applied. Next, for example, a layer 120 of an antimicrobial agent is applied. A layer 130 of the biocompatible controlled release polymer is then applied. These layers are repeated twice, for a total of three layers 120, 122, 124 of antimicrobial agent and three layers 130, 132, 140 of controlled release polymer (that do not contain active component). The thickness 121, 123, 125 of each antimicrobial agent layer 120, 122, 124 is the same. The thickness 131, 133 of the two internal controlled release polymer layers 130, 132 is also the same. However, the thickness 145 of the outermost controlled release polymer layer 140, which serves as the surface of the coating, is thicker. When embossed, two sets of regularly, semi-stochastically, or stochastically arranged features are formed in the outermost layer 140. Nanometer scale features 142 have a height 143 of one nanometer (nm) to less than 1000 nanometers. Micrometer scale features 144 have a height 145 of one micrometer (μm) to less than 1000 micrometers.

Turning now to the plan view of FIG. 2, it can be seen that the nanometer scale features 142 and the micrometer scale features 144 form a regularly, semi-stochastically, or stochastically arranged pattern on the surface of the coating 100 (indicated by dashed lines). This creates a surface structure that encourages osteoblast formation.

It is contemplated that in this embodiment of FIG. 1 and FIG. 2, the controlled release polymer is a silicone that absorbs water. As the water is absorbed in layer 140, the antimicrobial agent of layer 124 will diffuse out. Over time, polymer layer 132 will then become exposed to water and permit the antimicrobial agent in layer 122 to diffuse out. Finally, polymer layer 130 will then become exposed to water and permit the antimicrobial agent in layer 120 to diffuse out.

Figure 3:
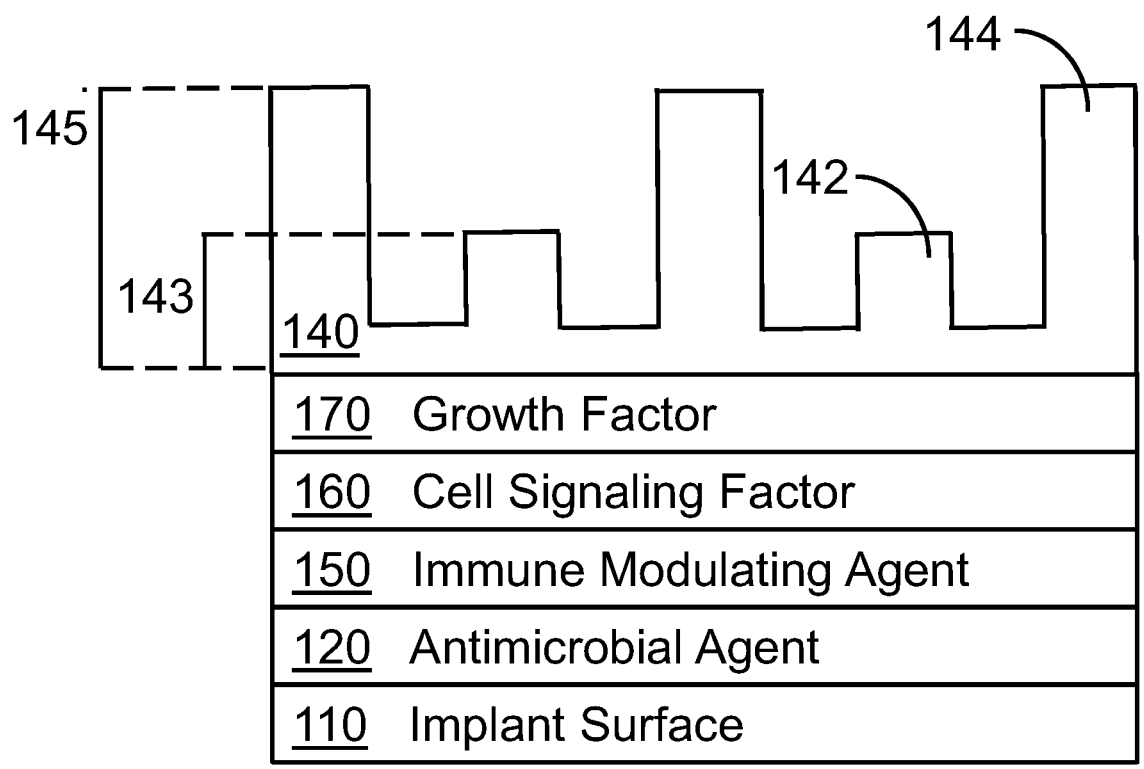
FIG. 3 is a cross-sectional view of a second example embodiment. The coating comprises a plurality of layers containing different active components and an outer layer of the controlled release polymer. Surface features are embossed into the outer layer.

A cross-sectional view of another embodiment is shown in FIG. 3. Here, the implant surface 110 serves as a substrate upon which several layers are applied. Next, a layer 120 of an antimicrobial agent is applied, then a layer 150 of an immune modulating agent, then a layer 160 of a cell signaling factor, then a layer 170 of a growth factor is applied. A layer 140 of the biocompatible controlled release polymer is then applied. When embossed, two sets of features are formed in the outermost layer 140. Nanometer scale features 142 have a height 143 of one nanometer (nm) to less than 1000 nanometers. Micrometer scale features 144 have a height 145 of one micrometer (μm) to less than 1000 nanometers.

It is contemplated that in this embodiment of FIG. 3, the controlled release polymer is a silicone that absorbs water. As the water is absorbed in layer 140, the antimicrobial agent of layer 120, the immune modulating agent of layer 150, the cell signaling factor of layer 160, and the growth factor of layer 170 can diffuse out at the same time. It is noted that these different active components may have different release rates due to their molecular size, concentration, etc.

Figure 4:
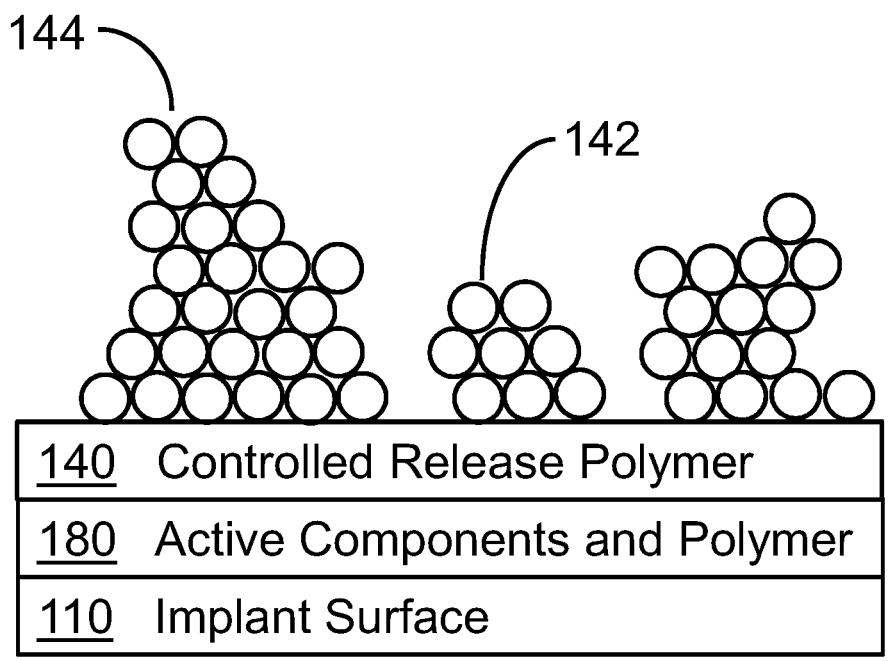
FIG. 4 is a cross-sectional view of a first example embodiment. The coating comprises a layer containing active component(s) and a controlled release layer. Surface features are formed by deposition upon the controlled release layer.

A cross-sectional view of yet another embodiment is shown in FIG. 4. Illustrated here is implant surface 110, which serves as a substrate. Located upon the surface is a layer 180 and a layer 140 of the biocompatible controlled release polymer. The single layer 180 is made of a biocompatible controlled release polymer in which one or more active components is dispersed. For example, the layer 180 can contain an antimicrobial agent, an immune modulating agent, a cell signaling factor, and a growth factor. Notably in this embodiment, the layer 140 can be relatively thin. The nanometer scale features 142 and the micrometer scale features 144 are formed by deposition of fibers through electrospinning (illustrated here as circles). The resulting surface features are not in a regular pattern (as illustrated in FIG. 2), but rather are chaotically placed and irregular. Multiple layers 180 could also be applied.

Figure 5:
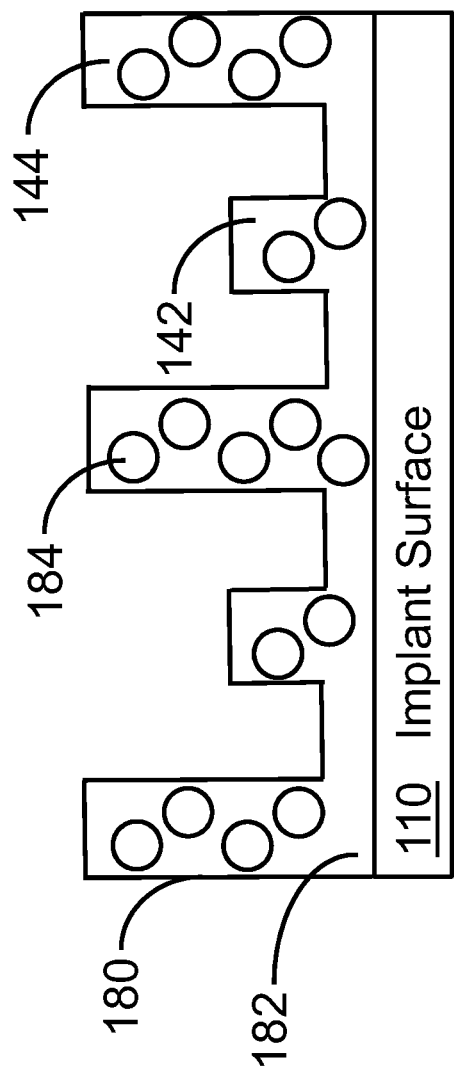
FIG. 5 is a cross-sectional view of a first example embodiment. The coating is a single layer made of a controlled release polymer and active component(s) dispersed therein.

A cross-sectional view of yet another embodiment is shown in FIG. 5. Illustrated here is implant surface 110, which serves as a substrate. Located upon the surface is a single layer 180. The single layer is made of a biocompatible controlled release polymer 182, in which at least one active component 184 (circles) is dispersed. The nanometer scale features 142 and the micrometer scale features 144 are present in the single layer 180. It is contemplated that in this embodiment, the polymer 182 will slowly dissolve upon exposure to water, releasing the active component(s) 184.

Combinations of the various features depicted in FIGS. 1-5 are also contemplated. The coating can be formed of multiple layers, with each layer having a separate construction. It should also be noted that while the substrate 110 in these figures is depicted as flat, that the substrate can have any shape. For example, the substrate upon which the controlled release coating is formed could be a ball joint that is part of a hip replacement.

This micro/nanofeatured polymer surface can improve stem cell integration while the controlled release polymer provides sustained bacterial kill by the sustained release of active components over a period of about three (3) weeks to about eight (8) weeks. Such sustained release allows for more sustained kill, which is valuable when the coating is applied to spacers used in revision surgeries, where antibiotics are administered for an extended time period until an infection is cleared.

It is particularly contemplated that a coating is formed from multiple layers, each layer containing a different antibiotic. A first line antibiotic could be released in a first phase, a second line antibiotic could be released in a second phase, etc. This multi-pronged release profile using different antibiotics should provide a greater degree of protection against multiple antibiotic resistant bacteria. It is also particularly contemplated that in some embodiments, the coating has multiple layers, with at least one layer containing one or more growth factors.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of forming a coating having a surface with exposed features thereon, comprising:

forming a coating upon a substrate; the coating comprising a biocompatible controlled release polymer and at least one active component; and depositing fibers onto an outermost surface of the coating to form the exposed features, wherein the features include micrometer scale features and nanometer scale features that rise above the outermost surface of the coating, and wherein the outermost surface is also exposed.

2. The method of claim 1, wherein the fibers are made of the biocompatible controlled release polymer.

3. The method of claim 1, wherein the substrate is the surface of an implant.

4. The method of claim 1, wherein the coating is formed by depositing a layer that comprises the biocompatible controlled release polymer and the at least one active component dispersed therein.

5. The method of claim 1, wherein the coating is formed by depositing a plurality of layers upon the substrate, with at least one layer containing the at least one active component, and a layer that comprises the biocompatible controlled release polymer forming the surface of the coating.

6. The method of claim 1, wherein the biocompatible controlled release polymer is a silicone, a polyester, or a polysaccharide.

7. The method of claim 1, wherein the biocompatible controlled release polymer is a silicone, a polyester, a polysaccharide, or a polyethylene glycol functionalized methacrylate.

8. The method of claim 1, wherein the at least one active component is an antimicrobial agent, an immune modulating agent, a cell signaling factor, a growth factor, a nutrient, or an antioxidant.

9. The method of claim 8, wherein the antimicrobial agent is an aminoglycoside; a glycoside antibiotic; a macrolide; a nitroimidazole; a tetracycline; a cephalosporin; a quinolone; a sulfonamide; a cyclic lipopeptide; a glycylcycline; an oxazolidinone; or a lipiarmycin.

10. The method of claim 8, wherein the immune modulating agent is imiquimod, resiquimod, or dexamethasone.

11. The method of claim 8, wherein the cell signaling factor is a cytokine.

12. The method of claim 8, wherein the growth factor is derived from platelet rich plasma; or is adrenomedullin; angiopoietin; a bone morphogenic protein (BMP); a colony stimulating factor (CSF); an epidermal growth factor (EGF); a fibroblast growth factor (FGF); a glial cell line-derived neurotrophic factor (GDNF); an insulin-like growth factor (IGF); or a transforming growth factor (TGF).

13. The method of claim 1, wherein the at least one active component comprises a plurality of different active components present in the coating.

14. A method of forming a coating having a surface with exposed features thereon, comprising:

forming a coating upon a substrate; the coating comprising a biocompatible controlled release polymer and at least one active component; and depositing fibers of the biocompatible controlled release polymer onto an outermost surface of the coating to form the exposed features, wherein the features include micrometer scale features and nanometer scale features that rise above the outermost surface of the coating, and wherein the outermost surface is also exposed.

* * * * *